United States Patent
Pomahac et al.

(10) Patent No.: US 10,251,669 B2
(45) Date of Patent: Apr. 9, 2019

(54) SYSTEMS AND METHODS FOR PREPARING TISSUE FLAPS

(71) Applicant: BRIGHAM AND WOMEN'S HOSPITAL, INC., Boston, MA (US)

(72) Inventors: Bohdan Pomahac, Dover, MA (US); Steve Pieper, Cambridge, MA (US)

(73) Assignee: Brigham and Women's Hospital, Inc., Boston, MA (US)

( * ) Notice: Subject to any disclaimer, the term of this patent is extended or adjusted under 35 U.S.C. 154(b) by 128 days.

(21) Appl. No.: 15/023,248

(22) PCT Filed: Sep. 23, 2014

(86) PCT No.: PCT/US2014/056889
§ 371 (c)(1),
(2) Date: Mar. 18, 2016

(87) PCT Pub. No.: WO2015/047979
PCT Pub. Date: Apr. 2, 2015

(65) Prior Publication Data
US 2016/0228143 A1    Aug. 11, 2016

Related U.S. Application Data

(60) Provisional application No. 61/881,482, filed on Sep. 24, 2013.

(51) Int. Cl.
| | |
|---|---|
| *G01N 1/00* | (2006.01) |
| *A61B 17/3211* | (2006.01) |
| *A61B 17/32* | (2006.01) |
| *A61B 17/322* | (2006.01) |
| *A61B 17/00* | (2006.01) |
| *A61B 17/30* | (2006.01) |

(52) U.S. Cl.
CPC .......... *A61B 17/3211* (2013.01); *A61B 17/32* (2013.01); *A61B 17/322* (2013.01); *A61B 2017/00792* (2013.01); *A61B 2017/00796* (2013.01); *A61B 2017/00969* (2013.01); *A61B 2017/306* (2013.01); *A61B 2017/320052* (2013.01)

(58) Field of Classification Search
CPC ....................................................... G01N 1/00
See application file for complete search history.

(56) References Cited

U.S. PATENT DOCUMENTS

| | | |
|---|---|---|
| 5,461,953 A | 10/1995 | McCormick |
| 7,442,192 B2 | 10/2008 | Knowlton |
| 8,702,686 B2 | 4/2014 | Geebelen et al. |
| 2008/0058603 A1 | 3/2008 | Edelstein et al. |

(Continued)

FOREIGN PATENT DOCUMENTS

WO    2013/045710 A1    4/2013

OTHER PUBLICATIONS

International Search Report and Written Opinion dated Mar. 10, 2015 in connection with PCT/US2014/056889.

*Primary Examiner* — Jyoti Nagpaul
(74) *Attorney, Agent, or Firm* — Quarles & Brady LLP

(57) ABSTRACT

A system and method for holding a cutting tool at a predetermined distance from a defined cutting surface to prepare a tissue flap of substantially uniform thickness for optimal viability. A tissue holder plate having a vacuum chamber is provided to stabilize the tissue mass, and a cutting tool holder and guide plate restrict the movement of the cutting tool with respect to the tissue holder plate.

19 Claims, 10 Drawing Sheets

(56) References Cited

U.S. PATENT DOCUMENTS

| | | |
|---|---|---|
| 2008/0249526 A1 | 10/2008 | Knowlton |
| 2010/0076473 A1 | 3/2010 | Tawfik et al. |
| 2010/0130991 A1 | 5/2010 | Levine |
| 2011/0238167 A1 | 9/2011 | Dove et al. |
| 2012/0165725 A1 | 6/2012 | Chomas et al. |
| 2013/0274778 A1 | 10/2013 | Mercier et al. |
| 2014/0046332 A1 | 2/2014 | Premanathan et al. |

SYSTEMS AND METHODS FOR PREPARING TISSUE FLAPS

CROSS-REFERENCE TO RELATED APPLICATIONS

This application represents the national stage entry of PCT International Application No. PCT/US2014/056889 filed Sep. 23, 2014, which claims priority to U.S. provisional patent application Ser. No. 61/881,482, filed Sep. 24, 2013, of which are incorporated by reference herein for all purposes.

STATEMENT REGARDING FEDERALLY SPONSORED RESEARCH

N/A

BACKGROUND OF THE INVENTION

The present invention relates to systems and methods for preparing a tissue flap from a tissue mass. More particularly, the invention relates to a system for preparing the tissue flap using a tissue holder plate to stabilize the tissue mass and a guide plate for translating a cutting tool in a predefined plane.

Tissue flaps are used and produced in many types of surgical procedures, particularly reconstructive surgery in a variety of indications to correct a multitude of tissue defects. For example, flaps may be used to cover (or can be created by incision in) a variety of wounds or resurface scars in the head, neck, extremities, and trunk or they may be employed to cover exposed tendons, bones, or major blood vessels. Tissue flaps may be used about the face where color match and contour are important or they may be used to close wounds having a poor blood supply as where wound circulation would not support a skin graft. A tissue flap traditionally refers to skin and subcutaneous tissue (or muscle, bone, or other tissue) along with the entire vascular plexuses, thereby bringing a large supply of tissue and an intact blood supply to the site of injury. Modern surgical techniques have expanded the traditional definition of a tissue flap to encompass free, microvascular flaps that may be anastomosed to an existing blood supply at or near the site of injury.

Tissue flaps are also produced during surgery. For example, tissue flaps are produced during breast reconstruction surgery wherein skin, fat, and the rectus muscle from the abdomen are removed and re-located to the chest to make the new breast. Similarly, tissue flaps can be produced temporarily during surgical procedures wherein surgical incisions are made in a patient.

Preparation of tissue flaps for the above mentioned surgeries require separation of tissue layers often across not well-defined anatomical planes using a cutting tool, such as a scalpel or an electrosurgical tool. Particularly when thin tissue flaps need to be developed, freehand surgical techniques commonly result in an inconsistent tissue flap thickness, leading to localized damage of blood supply and related healing complications. One non-limiting example of tissue flap preparation is the separation of skin and thin subcutaneous tissue from breast tissue during mastectomy, where the goal is to preserve viable skin for proper healing and reconstruction. When performed inaccurately, the resulting and often extensive skin necrosis results in prolonged healing and less effective reconstruction, often necessitating additional operations, and ultimately increasing the cost of care.

Therefore, there is a need for systems and methods to improve the creation and use of tissue flaps, for example, to improve the consistency of tissue flap creation.

SUMMARY OF THE INVENTION

The present invention overcomes the aforementioned drawbacks by providing a system and method to move a cutting tool within the bounds of a predetermined tissue plane so that the prepared tissue flap is of substantially uniform thickness for optimal viability. In particular, the present invention provides a tissue holder to stabilize, for example, the outer surface of the skin, and a tool holder and guide that restricts the movement of the cutting instrument with respect to the tissue holder.

In accordance with one aspect of the invention, a surgical device for preparing a tissue flap from a tissue mass is disclosed. The surgical device may include a guide plate having a planar slot or a peripheral ridge that surrounds the guide plate. The surgical device may further include a tissue holder plate defining a vacuum chamber configured to securely hold the tissue mass a predetermined distance from and orientation to the guide plate. A support handle may be coupled between the guide plate and the tissue holder plate. Additionally, a tool holder may be configured to receive a cutting tool for cutting the tissue flap from the tissue mass. The tool holder includes a tool holder plate coupled to a base. The tool holder plate may be dimensioned to engage the guide plate and translate or rotate within the peripheral ridge or slot to restrict movement of the cutting tool to a predefined plane relative to the tissue mass and the tissue holder plate. The tool holder further includes a guide arm coupled to the base of the tool holder at a predetermined angle relative to the tool holder plate and configured to engage the cutting tool. The movement of the tool holder plate within the peripheral ridge or slot of the guide plate enables the cutting tool to cut the tissue mass in the predefined plane at the predetermined angle, thereby preparing a tissue flap with a substantially uniform predetermined thickness from the tissue mass.

In accordance with another aspect of the invention a method for preparing a tissue flap from a tissue mass is disclosed. The method includes the steps of providing a guide plate including a peripheral ridge or a slot and attaching a vacuum chamber to a tissue holder plate. The tissue mass may be suctioned to the tissue holder plate a predetermined distance from the guide plate. A tool holder plate may be translated and rotated within the peripheral ridge or slot of the guide plate in a predefined plane and the tool holder plate may include a cutting tool attached thereto at a predetermined angle. The tissue mass may then be cut in the predefined plane at the predetermined angle to prepare the tissue flap with a substantially uniform thickness from the tissue mass.

In accordance with another aspect of the invention a surgical device for preparing a tissue flap from a tissue mass is disclosed. The surgical device includes an electro-mechanical actuator in communication with a computer controller having stored thereon a control algorithm. The surgical device further includes a tissue holder plate configured to securely hold the tissue mass a predetermined distance from and orientation to the electro-mechanical actuator. A support member is coupled between the electro-mechanical actuator and the tissue holder plate, and a tool holder is coupled to the electro-mechanical actuator and configured to receive a cutting tool for cutting the tissue flap from the tissue mass. The control algorithm is configured to restrict movement of the cutting tool to a predefined range of motion relative to the tissue mass and the electro-mechanical actuator in order to enable the cutting tool to cut the tissue mass in the predefined range of motion, thereby preparing a tissue flap with a substantially uniform predetermined thickness from the tissue mass.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
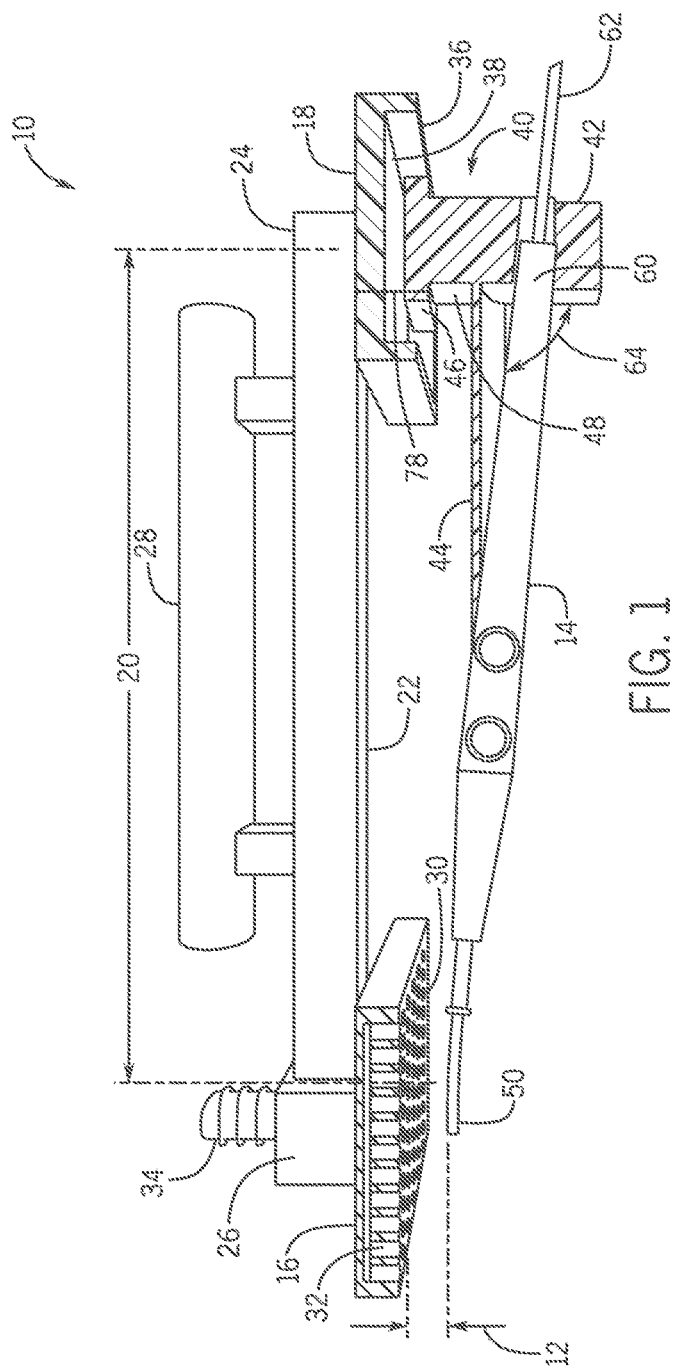
FIG. 1 is a plan view of an example surgical device including a tool holder holding a cutting tool, a guide plate, and a tissue holder plate according to one embodiment of the present invention.
Figure 2:
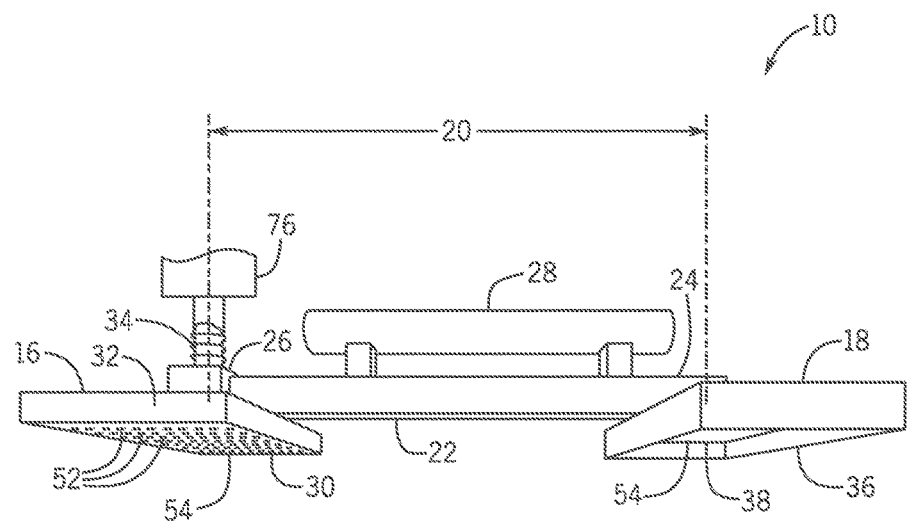
FIG. 2 is a perspective view of the example surgical device of FIG. 1 including a vacuum chamber and a vacuum hose attachment for providing suction to a tissue mass according to one embodiment of the present invention.

Referring particularly now to FIGS. 1 and 2, a surgical device 10 is shown that is configured to prepare a tissue flap (not shown), having a substantially uniform thickness 12, from a tissue mass (not shown) using a cutting tool 14 during surgery. The surgery may be, for example, a mastectomy, a reconstructive surgery, a facelift, a thin flap evaluation in mastectomy, a general flap elevation, or any other surgical procedure where a tissue flap of generally uniform thickness may be advantageous. The surgical device 10 may be disposable or non-disposable, and may include, for example, a tissue holder plate 16 and a guide plate 18 spaced a predetermined distance 20 apart. The predetermined distance 20 may be determined by the length of a support member 22 having a proximal end 24 and a distal end 26. A support handle 28 may extend proximate to the proximal end 24 and extend toward the distal end 26 of the support member 22 and may be coupled thereto.

The tissue holder plate 16 may be coupled to the distal end 26 of the support member 22 and include a perforated plate 30 and a vacuum chamber 32 for suctioning the tissue mass. The vacuum chamber 32 may extend from a vacuum hose attachment 34 through the support member 22, and into the tissue holder plate 16 and through the perforated plate 30. The guide plate 18 may be coupled to the proximal end 24 of the support member 22 and include a peripheral ridge 36 surrounding the edges, thereby creating a predefine plane 38.

The predefined plane 38 of the guide plate 18 may be configured, for example, to receive a tool holder 40 capable of translating and rotating within the predefined plane 38. The tool holder 40 may include a base 42 configured to receive the cutting tool 14. A guide arm 44 may be coupled to the base 42 and configured to restrict lateral movement of the cutting tool 14. Attached to a top portion 48 of the base 42 may be a tool holder plate 46. The tool holder plate 46 may be configured, for example to translate or rotate within the predefined plane 38 defined by the peripheral ridge 36 of the guide plate 18 so that a tip 50 of the cutting tool 14 moves in a defined planar region to cut the tissue flap with the substantially uniform thickness 12.

Referring particularly to FIG. 2, the surgical device 10, in absence of the tool holder 40, which will be described in further detail below, is shown. The tissue mass may be held, for example, by the perforated plate 30 attached to the vacuum chamber 32 so that the tissue mass is held at the predetermined distance 20 and in geometric relationship to the guide plate 18. Suction may be provided through the vacuum hose attachment 34, and the amount of suction may be controlled via a valve system 76 to adjust the amount of suction, and to release the suction, when the cutting operation is complete. The perforated plate 30 may include circular perforations 52 of various diameters and positioned in various distributions depending on the particular surgical procedure, the anatomy of the patient or the needs of the tissue mass fixation. In an alternative embodiment, the perforations 52 may be of any suitable geometric shape or size required for suction of the tissue mass, or the perforations 52 may be replaced, or used in conjunction, with any suitable interface to enhance the suction capability.

Figure 3:
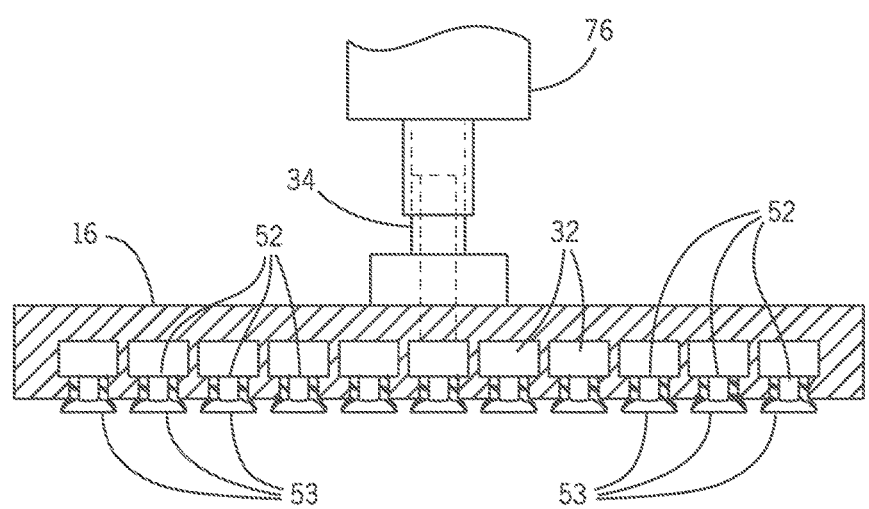
FIG. 3 is a perspective view of the tissue holder plate including suction cups for providing suction to a tissue mass according to one embodiment of the present invention.

For example, in the embodiment shown in FIG. 3, the tissue holder plate 16 includes a plurality of suction cups 53 extending from each one of the perforations 52. Thus, each suction cup 53 includes an opening to create a passageway from the suction cup 53 to the vacuum chamber 32 to hold the tissue mass in geometric relationship to the guide plate 18. The suction cups 53 may be constructed from a soft, rubber material, however any suitable material may be used. Suction may be provided through the vacuum hose attachment 34 such that each suction cup 53 coupled to the perforations 52 could minimize loss of negative pressure due to an imperfect seal between the tissue holder plate 16 material and the surface of the tissue mass.

In one non-limiting example, the suction provided through the vacuum hose attachment 34 to hold the tissue mass in place may be used in conjunction with, or replaced by, a surgical glue or gel to secure the tissue mass to the tissue holder plate 16. The surgical glue and/or gel may be advantageous to secure the tissue mass, as during some surgical procedures, the cutting tool 14 (e.g., a bovie) can reach high temperatures and cause damage to the tissue. In one non-limiting example, the glue and/or gel may be provided in the form of a liquid that is directly applied to the tissue holder plate 16 and/or the patient's skin. Alternatively, the glue may be provided in the form of a double-sided adhesive patch (not shown) that may be applied to the tissue holder plate 16. The properties of the double-sided adhesive patch could securely hold the tissue mass during the cutting operations, but may be peeled away easily from the tissue mass and the tissue holder plate 16 when cutting is complete. In one embodiment, the double-sided adhesive patch may be disposable so that a fresh patch can be used for each cutting procedure or the patch may be used for two or more tissue areas prior to being replaced. In a further embodiment, the adhesive patch may also include areas that operate like suction cups, similar to the suction cups 53 previously described, that interface with the vacuum chamber 32 so that the suction and adhesive are complementary. Further, the double-sided adhesive patches may be provided in sterile packages in suitable quantities for the target procedures and may be sized to match the geometry of the tissue holder plate 16.

In addition, a surgical gel or other compound may help maintain thermal stability of the tissue. Depending on the procedure, it may be advantageous for the glue to contain pharmaceutical compounds or other ingredients that help promote tissue viability. Alternatively, hook-like devices (not shown) may be coupled to the tissue holder plate 16 to grasp the tissue securely. The hook-like devices could be used with the surgical glue or gel and/or with the vacuum hose attachment 34, or all together.

The dimensions of the perforated plate 30, as well as the tissue holder plate 16, the guide plate 18, the support member 22, and the support handle 28, for example, may also be varied according to the needs of the particular surgical procedures and/or the anatomy of the patient. The anatomy of the patient, for example, may not be flat, but rather curved or shaped based on the application. In one non-limiting example, the perforated plate 30, the tissue holder plate 16 and the guide plate 18 may be rectangular in shape and have dimensions of, for example, 2 inches by 3 inches. The support handle 28 may be approximately 6 inches in length and the support member 22 may be approximately 10 inches in length for preparation of tissue flaps during mastectomy. Alternatively, the perforated plate 30, the tissue holder plate 16 and the guide plate 18 may have proportionately smaller dimensions, and the support member 22 and the support handle 28 may be proportionately shorter in length for procedures, such as reconstructive surgery of facial features. The length of the support member 22, therefore, may determine the predetermined distance 20 between the guide plate 18 and the tissue holder plate 16.

The perforated plate 30, the tissue holder plate 16 and the guide plate 18 are not limited to the rectangular dimensions provided above. In an alternative embodiment, the perforated plate 30, the tissue holder plate 16 and the guide plate 18 may be of any suitable geometric shape, for example square, circular, ring shaped, curved in three-dimensions or any combination thereof. Further, the perforated plate 30, the tissue holder plate 16 and the guide plate 18 can be constructed of any suitable medical grade material such as stainless steel, plastic, titanium or rubber polymers. FIG. 2 shows planar surfaces 54 for the perforated plate 30, the tissue holder plate 16 and the guide plate 18. However, in an alternative embodiment the perforated plate 30, the tissue holder plate 16 and the guide plate 18 may have non-linear surfaces (not shown) to better conform to anatomy and to customize the resulting tissue flap shape to meet clinical targets, for example. In a particular non-limiting example, the surfaces of the perforated plate 30, the tissue holder plate 16, and the guide plate 18 may be parallel to the support member 22 along any cross section along the axis parallel to the support member 22, but have a semi-circular cross section along the axis perpendicular to support member 22.

In another example, it may be advantageous for the shape of the cutting plane 54 to closely conform to the anatomical contours of a particular patient's anatomy. There exist in the art techniques to determine this anatomical surface information, for example through the use of medical imaging techniques such as CT or MR scanning and subsequent post-processing. Well known techniques exist for creating physical objects based on this geometry, for example through computer controlled milling or 3D printing. Thus, the exact shape and size of the guide plates 16, 18 may be determined based on patient-specific measurement information.

In another example, it may be advantageous to select the shape of the guide plates 16, 18 based on the particular surgical procedure to be performed. For example, a surgeon may determine that a nipple-sparing mastectomy procedure is appropriate for the patient and, through the use of medical imaging and custom manufacturing, a patient-specific and procedure-specific surface geometry may be defined. Such patient-specific and/or procedure-specific custom instrumentation may include, for example, a tissue holder 16 that encompasses the entire target anatomical structure, such as a tissue holder that holds the entire breast. Alternatively, the tissue holder 16 may include multiple sections that are used sequentially or in parallel to carry out the required steps of the surgical procedure.

Figure 4:
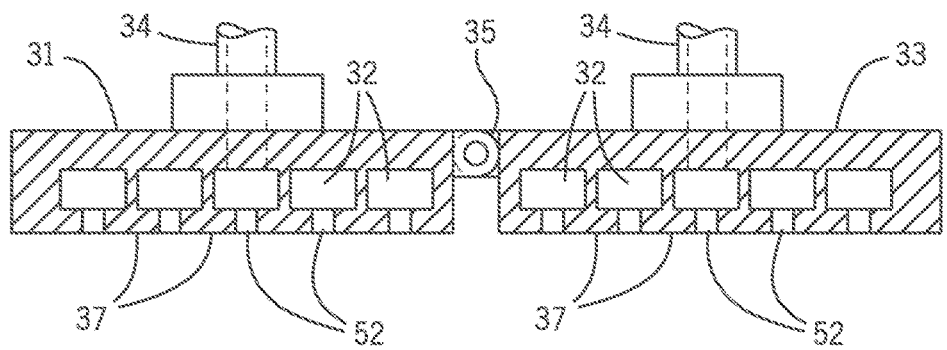
FIG. 4 is a perspective view of the tissue holder plate including one or more sub-plates according to one embodiment of the invention.

In yet another non-limiting example, the perforated plate 30 and the tissue holder plate 16 may be composed of two or more sub-plates 31, 33, as shown in FIG. 4. Each sub-plate 31, 33 may be a perforated plate, similar to the perforated plate 30, and include independent vacuum chambers 32 for suctioning the tissue mass. The sub-plates may include a hinge 35, for example, that allows the sub-plates to fold back from the patient when not needed. In addition, when folded into place, the sub-plates 31, 33 may be configured to lock, such that the combination of the sub-plates 31, 33 are rigid and form a solid base for holding the tissue and supporting exact tissue dissection. The sub-plates 31, 33 may further include one or more support posts 37 that extend between the perforations 52 in the vacuum chamber 32.

Additionally, or alternatively, the perforated plate 30 and the tissue holder plate 16 may be composed of multiple strips of sub-plates, such that an exact length of the tissue holder plate 16 and the perforated plate 30 could be controlled. Thus, a range of standard tissue holder plate 16 sizes may be used during different parts of a surgical procedure depending on the portion of the tissue, such as breast tissue, being prepared.

Similarly, the support handle 28 may be of any suitable geometric shape. For example, the support handle 28 is shown in FIG. 2 with a cylindrical handle so that the surgeon may easily manipulate the surgical device 10 and tissue mass during the procedure. The precise shape of the support handle 28 may be readily adapted for better ergonomics, for example, depending on the overall size of the tissue mass to be manipulated. Further, the support handle 28 may be constructed of any suitable medical grade material such as plastic, titanium or rubber polymers.

Figure 5:
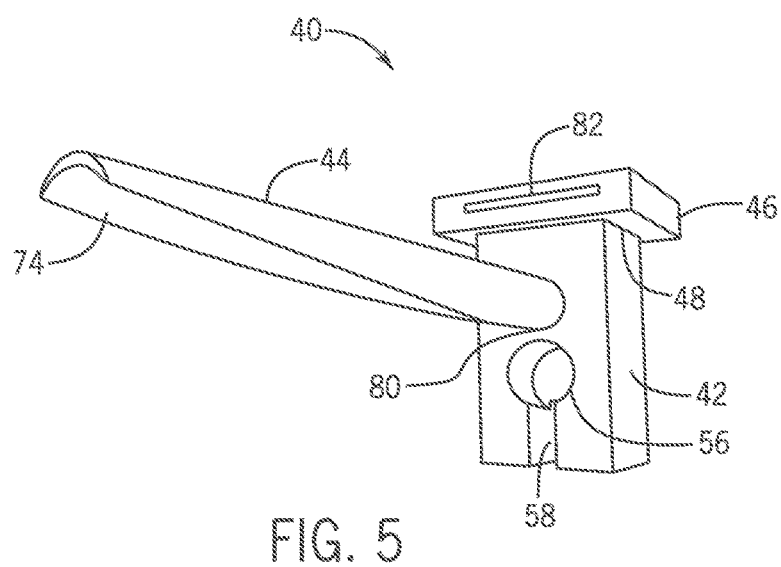
FIG. 5 is a perspective view of the tool holder of FIG. 1 including a base, a tool holder plate, and a guide arm according to one embodiment of the present invention.

Turning now to FIG. 5, the tool holder 40 is shown. As previously described, the tool holder plate 46 of the tool holder 40 is configured to translate and rotate within the predefined plane 38 defined by the peripheral ridge 36 of the guide plate 18 so that the tip 50 of the cutting tool 14, as shown in FIG. 1, moves in a defined planar region to cut the tissue flap with the substantially uniform thickness 12. Alternatively, the tool holder plate 46, the tissue holder plate 16, and the guide plate 18 may be in the shape of a half cylinder, for example, so that the tissue holder plate 16 better fits the anatomical form of the target tissue. As the tool holder 40 translates within the predefined half cylinder surface (not shown), the tissue flap being cut follows the three-dimensional body contour while preserving the uniform tissue thickness. The tool holder plate 46 may be any suitable size (e.g., 1 inch by 1 inch, or 2 inches by 1 inch) and geometric shape (e.g., square, rectangular or circular) to allow movement within the area defined by the peripheral ridge 36 around the guide plate 18. Further, the tool holder 40 can be constructed of any suitable medical grade material such as plastic, titanium or rubber polymers. The size and shape of the tool holder 40 may be adjusted according to the particular surgical procedure, the anatomy of the patient or the needs of the tissue mass fixation.

The base 42 of the tool holder 40 may include an aperture 56, for example a circular aperture, and a cord slot 58 configured to receive a base 60 of the cutting tool 14 and a cord 62 of the cutting tool 14, as shown in FIG. 1, respectively. The guide arm 44 may be fixed to the base 42 or attached to the base 42 with a sliding linkage 80, as shown in FIG. 5, that is configured to slide vertically, and therefore the cutting tool 14 is slid vertically as well, to select the substantially uniform thickness 12 of the tissue flap. Alternatively, the tool holder 40 may be custom fabricated based on the cutting tool 14. The guide arm 44 may be, for example, a cylindrical cut out 74 as shown in FIG. 5. The shape of the aperture 56, the cord slot 58, and the guide arm 44 may vary depending on the type of cutting tool 14 being used (i.e., a scalpel, an electrosurgical tool, a pencil, scissors, or a Bovie knife). Alternatively, the guide arm may be a clamp or other mechanical attachment. The guide arm 44 may be coupled to the base 42 of the tool holder 40 to form a predetermined angle 64 at which the cutting tool 14 is held, as shown in FIG. 1, with respect to the tissue mass. The predetermined angle 64 can be adjusted, for example, by the geometric design of the guide arm 44 and how the guide arm 44 is attached to the base 42.

In one example, the predetermined angle 64 may be adjustable at the time of the procedure by including a hinge-like mechanism (not shown) that allows the angle 64 to be set and locked in place as needed. The hinge-like mechanism may be configured to be releasable during the procedure to facilitate a more free-hand movement of the tool holder 40, while allowing the tool holder 40 to be re-locked to the original predefine angle 64, for example by including markings on the hinge so that the correct angle can be easily set.

In some embodiments, the cutting tool 14, similar to the tool holder 40, may also be custom fabricated. For example, the cutting tool 14 may be a custom tool with multiple functions, such as a forward facing scalpel blade that has integrated cautery functionality. Thus, when a bleed occurs, the cautery could be applied without removing the cutting tool 14. Alternatively, suction may be integrated into the cutting tool 14, such that the tissue mass could be cut, and then blood may be suctioned away prior to applying cautery, again without removing the cutting tool 14. In yet another embodiment, a wedge (not shown) may be used hold the tissue mass, such as breast gland tissue, away from the cutting surface. The wedge may provide some tension at the site of the dissection, and could use one or more of the tissue fixation techniques (e.g., vacuum, hooks, surgical glue, etc.), as previously described, to firmly hold the tissue mass. In addition, the cutting tool 14 may be custom fabricated to include a video camera or endoscope, for example, to provide visualization when operating deep within the tissue mass, for example near the chest wall in mastectomy of a large breast.

Figure 6A:
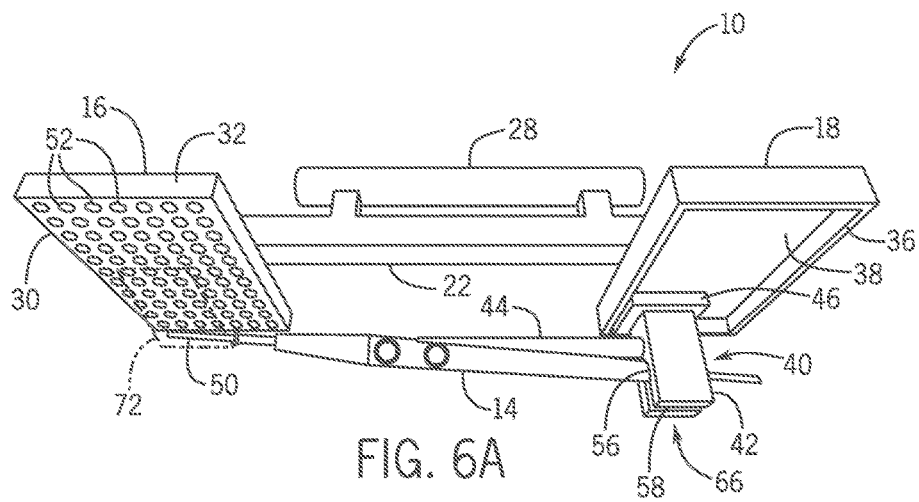
FIGS. 6A-6D are perspective views of the tool holder of FIG. 1 being translated within a predefined plane of the guide plate according to one embodiment of the present invention.
Figure 6B:
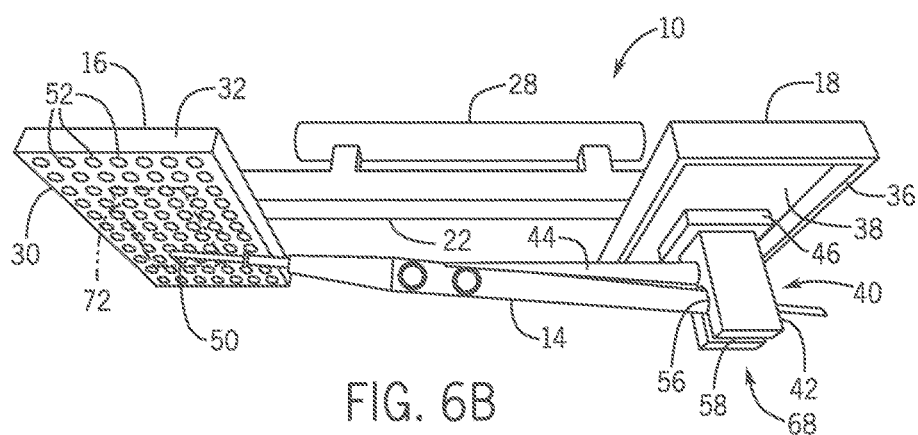
Figure 6C:
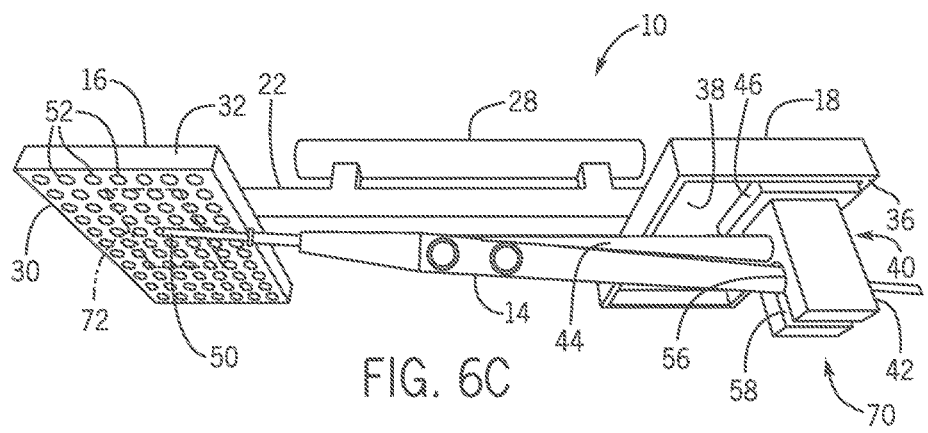
Figure 6D:
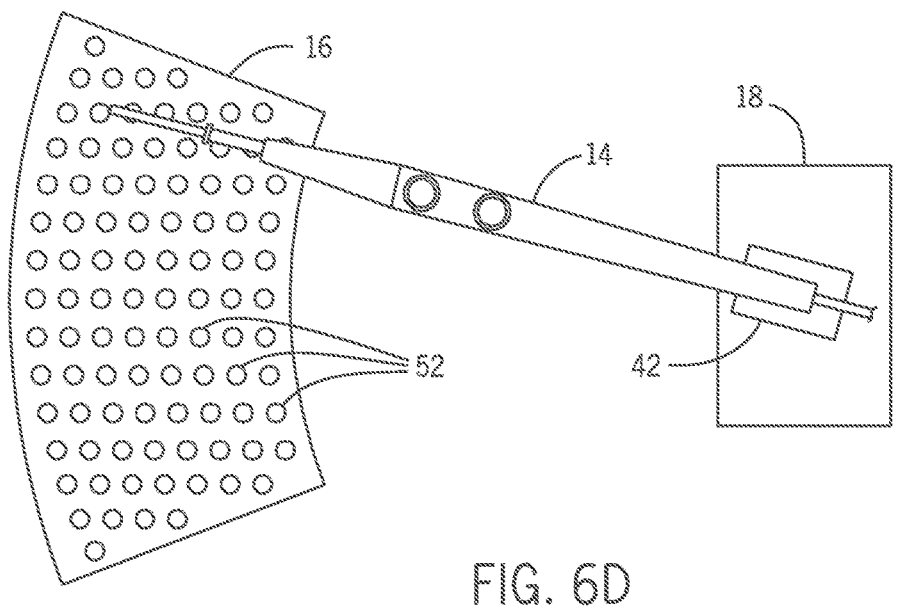

Turning now to FIGS. 6A-6D illustrations of the relative motion of the tool holder 40, and more specifically, the tool holder plate 46, in the predefined plane 38 with respect to the guide plate 18 and the tissue holder plate 16 is shown. As the tool holder 40 is moved from a first position 66, as shown in FIG. 6A, in the predefined plane 38, to a second position 68, as shown in FIG. 6B, for example, the tool holder plate 46 slides relative to the guide plate 18 while maintaining the substantially uniform thickness 12 of the tissue flap. The tool holder 40 may be moved from the second position 68, as shown in FIG. 6B to a third position 70, as shown in FIG. 6C, for example while still maintaining the substantially uniform thickness 12 of the tissue flap being cut by the cutting tool 14. As the tool holder 40 is moved among the exemplary positions, the tool holder 40 may also be rotated, as shown in FIG. 6D, within the predefined plane 38 while maintaining the substantially uniform thickness 12 of the tissue flap. Also shown in FIG. 6D is the tissue holder plate 16 having a non-rectangular shape which may be advantageous for certain procedures.

In addition, as the tool holder 40 is moved among the exemplary positions, as shown in FIGS. 6A-6D, within the predefined plane 38, a cutting plane 72 is defined about the tissue mass being held in place by the tissue holder plate 16. The cutting plane 72 is therefore defined by the relative dimensions of the tool holder plate 46 and the guide plate 18. It will be appreciated that the relative size of the cutting plane 72 can be varied according to the selected dimensions of guide plate 18 or the tool holder plate 46, or a combination thereof.

In an alternative embodiment, the guide plate 18 and the tool holder plate 46 may be attached such that they remain in approximation while the tool holder 40 is moved among the first position 66, the second position 68, and the third position 70, as shown in FIGS. 6A, 6B and 6C, respectively. For example, a linkage 78, as shown in FIG. 1, could be used to hold the guide plate 18 and the tool holder plate 46 together while allowing freedom of movement within the two-dimensional predefined plane 38. Note, however, the tool holder 40 is not restricted to the positions shown in FIGS. 6A-6C, but may move to any position within the predefined plane 38. As a non-limiting example, the linkage 78 between the tool holder plate 46 and the guide plate 18 may be accomplished by embedding a magnet 82, as shown in FIG. 5, of suitable strength in the tool holder plate 46 and forming the guide plate 18 out of steel or any other suitable material attracted to the magnet. Through selection of appropriate magnetic strengths and controlling for the frictional properties of the materials, the tool holder plate 46 and the guide plate 18 can be made to slide easily through all positions within the predefined plane 38, while remaining stably attached to ensure that the substantially uniform thickness 12 is maintained during the cutting and tissue manipulation processes. As another non-limiting example, the linkage 78 between tool holder plate 46 and guide plate 18 may be accomplished through the use of articulating arms constructed so as to ensure that the guide plate 18 remains in approximation with the tissue holder plate 16 while allowing free motion within the predefined plane 38.

Figure 7:
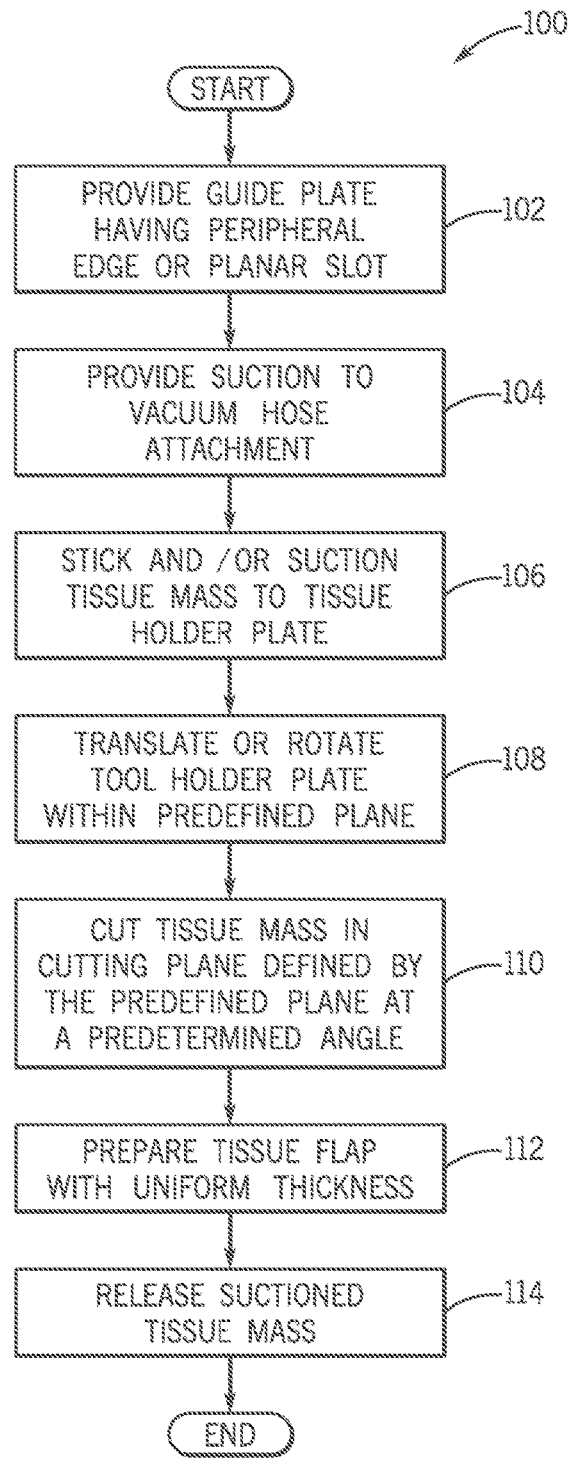
FIG. 7 is a flow chart setting forth the steps of processes for creating a tissue flap from a tissue mass in accordance with the present invention.

Referring now to FIG. 7, a flow chart setting forth exemplary steps 100 for preparing the tissue flap from the tissue mass is provided. To start the process, the guide plate 18 is provided at process block 102. The guide plate 18 includes a peripheral ridge or a planar slot that determines the predefined plane 38 wherein the tissue mass may be cut. At process block 104, external suction may be provided through the vacuum hose attachment 34, and the amount of suction may be controlled via the valve system 76 to adjust the amount of suction in the vacuum chamber 32. The vacuum chamber 32 may provide suction to suction the tissue mass to the tissue holder plate 16 at process block 106. As previously described, the tissue holder plate 16 may include a perforated plate 30 for suctioning the tissue mass to the tissue holder plate 16. At process block 108, the tool holder 40 is translated and/or rotated within the predefined plane 38. The tissue mass is cut in the cutting plane 72 that is defined by the predefined plane 38, as previously described, at process block 110. The tissue flap is prepared with the substantially uniform thickness 12 at process block 112. Once the tissue flap is completely cut from the tissue mass at process block 112, the suction provided by the vacuum chamber 32 is released to end the procedure at process block 114.

Figure 8:
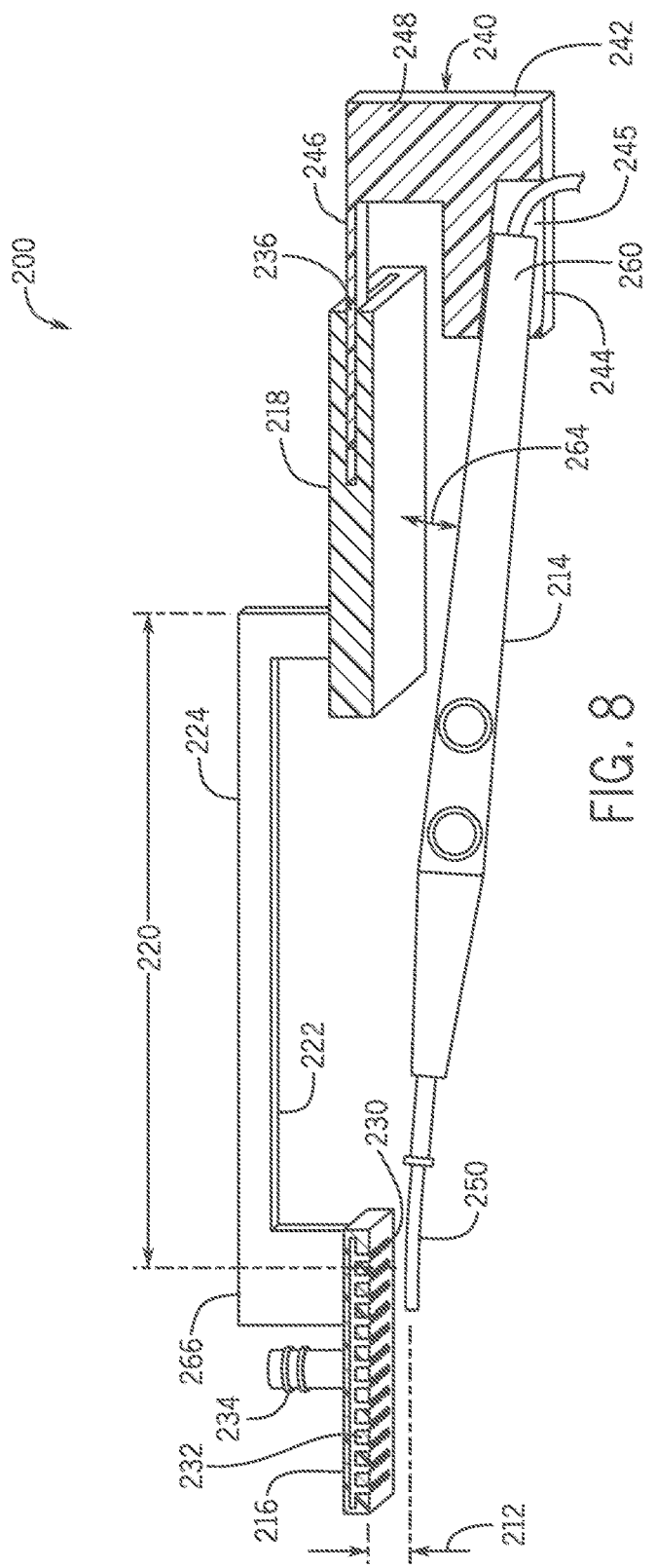
FIG. 8 is a plan view of another example surgical device including a tool holder holding a cutting tool, a guide plate, and a tissue holder plate according to one embodiment of the present invention.
Figure 9:
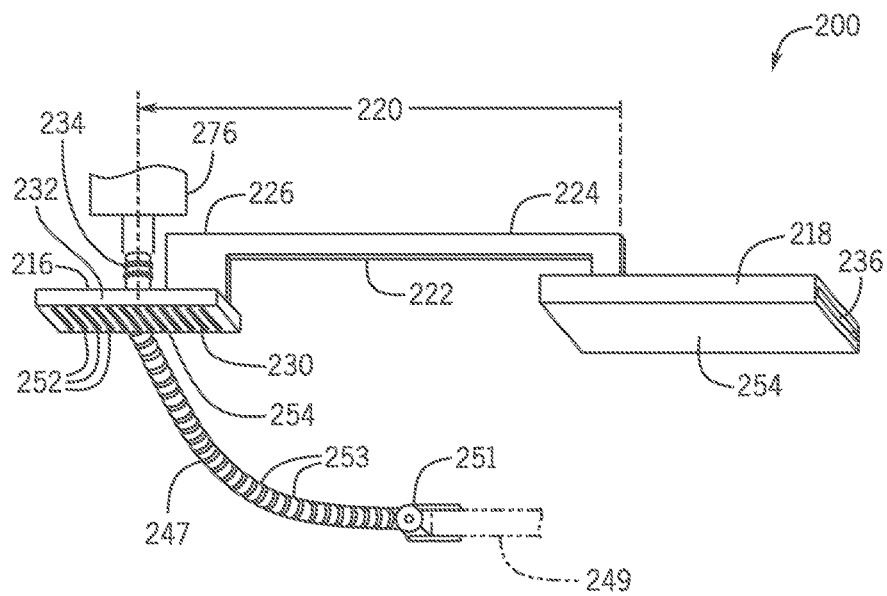
FIG. 9 is a perspective view of the example surgical device of FIG. 8 including a vacuum chamber, a vacuum hose attachment for providing suction to a tissue mass, and a support arm according to one embodiment of the present invention.

Referring particularly now to FIGS. 8 and 9, another exemplary surgical device 200, similar to the previously described surgical device 10, is shown. The surgical device 200 is configured to prepare a tissue flap (not shown), having a substantially uniform thickness 212, from a tissue mass (not shown) using a cutting tool 214 during surgery. The surgery may be, for example, a mastectomy, a reconstructive surgery, a facelift, a thin flap evaluation in mastectomy, a general flap elevation, or any other surgical procedure where a tissue flap of generally uniform thickness may be advantageous. The surgical device 200 may be disposable or non-disposable, and may include, for example, a tissue holder plate 216 and a guide plate 218 spaced a predetermined distance 220 apart. The predetermined distance 220 may be determined by the length of a support member 222 having a proximal end 224 and a distal end 226. The support member 222 may also be used as a support handle for a user to grasp, for example.

The tissue holder plate 216 may be coupled to the distal end 226 of the support member 222 and include a perforated plate 230 and a vacuum chamber 232 for suctioning the tissue mass. The vacuum chamber 232 may extend from a vacuum hose attachment 234, into the tissue holder plate 216 and through the perforated plate 230. The guide plate 218 may be coupled to the proximal end 224 of the support member 222 and include a slot 236 on a bottom surface of the guide plate 218, thereby creating a predefined plane 238. In an alternative embodiment, the slot 236 may be positioned on a top surface of the guide plate 218.

The predefined plane 238 of the guide plate 218 may be configured, for example, to receive a tool holder 240 capable of translating and rotating within the predefined plane 238. The tool holder 420 may include a base 242 configured to receive the cutting tool 214. A guide arm 244, having an aperture 245 for receiving the cutting tool 214, may be coupled to the base 242 and configured to restrict lateral movement of the cutting tool 214. Attached to a top portion 248 of the base 242 may be a tool holder plate 246, which may be in the form of a tongue, for example. The tool holder tongue 246 may be received in the slot 236 of the guide plate 218 and configured, for example to translate and rotate within the predefined plane 238 defined by the slot 236 of the guide plate 218 so that a tip 250 of the cutting tool 214 moves in a defined planar region to cut the tissue flap with the substantially uniform thickness 212. In some embodiments, the tip 250 of the cutting tool 214 may be curved, as shown in FIG. 8, such that the cutting plane is substantially parallel to the tissue holder plane, which is defined by the tissue holder plate 216.

Referring particularly to FIG. 9, the surgical device 200, in absence of the tool holder 240, which will be described in further detail below, is shown. The tissue mass may be held, for example, by the perforated plate 230 attached to the vacuum chamber 232 so that the tissue mass is held at the predetermined distance 220 and in geometric relationship to the guide plate 218. A support arm 247 may be provided in order to attach the surgical device 200 to a surface 249, such as an operating room table. The support arm 247, at one end, may be coupled to the tissue holder plate 216. A securing mechanism 251, such as a clamp, may be coupled to an opposing end of the support arm 247 to secure the surgical device 200 to the operating room table 249. Thus, the clinician can have the tissue mass securely held in place along with the surgical device 200 and allowing one hand to be used to move the cutting tool 214 and the other hand to be used to hold the tissue mass, such as breast gland tissue.

In some embodiments, the support arm 247 includes a plurality of loose parts 253 that are hingeable with respect to one another. The plurality of loose parts 253 maybe connected, for example, by a flexible tension rod (not shown) extending through a central bore of the support arm 247. Thus, the support arm 247 can be adjusted and locked in any desired position with respect to the tissue mass. It is also possible to place the tissue holder plate 216 in a precise location relative to the tissue mass. Once the support arm 247 and surgical device 200 are adjusted to the desired position, the position can be fixed by locking the flexible tension rod. In one non-limiting example, the support arm 247 can be detachable from the tissue holder plate 216 of the surgical device 200, or alternatively, the support arm 247 may be permanently attached to the surgical device 200.

Once the support arm 247 and surgical device 200 are in the desired position, suction may be provided through the vacuum hose attachment 234, and the amount of suction may be controlled via a valve system 276 to adjust the amount of suction, and to release the suction, when the cutting operation is complete. The perforated plate 230 may include circular perforations 252 of various diameters and positioned in various distributions depending on the particular surgical procedure, the anatomy of the patient or the needs of the tissue mass fixation. In an alternative embodiment, the perforations 252 may be of any suitable geometric shape or size required for suction of the tissue mass, or the perforations 252 may be replaced, or used in conjunction, with any suitable interface to enhance the suction capability.

For example, as previously described with respect to FIG. 3, the tissue holder plate 216 may include the plurality of suction cups 53 extending from each one of the perforations 52. Thus, each suction cup 53 includes an opening to create a passageway from the suction cup 53 to the vacuum chamber 32 to hold the tissue mass in geometric relationship to the guide plate 18. The suction cups 53 may be constructed from a soft, rubber material, however any suitable material may be used. Suction may be provided through the vacuum hose attachment 34 such that each suction cup 53 coupled to the perforations 52 could minimize loss of negative pressure due to an imperfect seal between the tissue holder plate 216 material and the surface of the tissue mass.

In one non-limiting example, the suction provided through the vacuum hose attachment 234 to hold the tissue mass in place may be used in conjunction with, or replaced by, a surgical glue or gel to secure the tissue mass to the tissue holder plate 216. The surgical glue and/or gel may be advantageous to secure the tissue mass, as during some surgical procedures, the cutting tool 214 (e.g., a bovie) can reach high temperatures and cause damage to the tissue. In one non-limiting example, the glue and/or gel may be provided in the form of a liquid that is directly applied to the tissue holder plate 216 and/or the patient's skin. Alternatively, the glue may be provided in the form of a double-sided adhesive patch (not shown) that may be applied to the tissue holder plate 216. The properties of the double-sided adhesive patch could securely hold the tissue mass during the cutting operations, but may be peeled away easily from the tissue mass and the tissue holder plate 216 when cutting is complete. In one embodiment, the double-sided adhesive patch may be disposable so that a fresh patch can be used for each cutting procedure or the patch may be used for two or more tissue areas prior to being replaced. In a further embodiment, the adhesive patch may also include areas that operate like suction cups, similar to the suction cups 53 previously described, that interface with the vacuum chamber 232 so that the suction and adhesive are complementary. Further, the double-sided adhesive patches may be provided in sterile packages in suitable quantities for the target procedures and may be sized to match the geometry of the tissue holder plate 216.

In addition, a surgical gel or other compound may help maintain thermal stability of the tissue. Depending on the procedure, it may be advantageous for the glue to contain pharmaceutical compounds or other ingredients that help promote tissue viability. Alternatively, hook-like devices (not shown) may be coupled to the tissue holder plate 216 to grasp the tissue securely. The hook-like devices could be used with the surgical glue or gel and/or with the vacuum hose attachment 234, or all together.

The dimensions of the perforated plate 230, as well as the tissue holder plate 216, the guide plate 218, and the support member 222, for example, may also be varied according to the needs of the particular surgical procedures and/or the anatomy of the patient. The anatomy of the patient, for example, may not be flat, but rather curved or shaped based on the application. In one non-limiting example, the perforated plate 230, the tissue holder plate 216 and the guide plate 218 may be rectangular in shape and have dimensions of, for example, 2 inches by 3 inches. The support member 222 may be approximately 10 inches in length for preparation of tissue flaps during mastectomy. Alternatively, the perforated plate 230, the tissue holder plate 216 and the guide plate 218 may have proportionately smaller dimensions, and the support member 222 may be proportionately shorter in length for procedures, such as reconstructive surgery of facial features. The length of the support member 222, therefore, may determine the predetermined distance 220 between the guide plate 218 and the tissue holder plate 216.

As previously described, the perforated plate 230, the tissue holder plate 216 and the guide plate 218 are not limited to the rectangular dimensions provided above. In an alternative embodiment, the perforated plate 230, the tissue holder plate 216 and the guide plate 218 may be of any suitable geometric shape, for example square, circular, curved in three-dimensions or any combination thereof. Further, the perforated plate 230, the tissue holder plate 216 and the guide plate 218 can be constructed of any suitable medical grade material such as stainless steel, plastic, titanium or rubber polymers. FIG. 9 shows planar surfaces 254 for the perforated plate 230, the tissue holder plate 216 and the guide plate 218. However, in an alternative embodiment the perforated plate 230, the tissue holder plate 216 and the guide plate 218 may have non-linear surfaces (not shown) to better conform to anatomy and to customize the resulting tissue flap shape to meet clinical targets, for example. In a particular non-limiting example, the surfaces of the perforated plate 230, the tissue holder plate 216, and the guide plate 218 may be parallel to the support member 222 along any cross section along the axis parallel to the support member 222, but have a semi-circular cross section along the axis perpendicular to support member 222.

In yet another non-limiting example, the perforated plate 230 and the tissue holder plate 216 may be composed of two or more sub-plates, such as the sub-plates shown in FIG. 4. Each sub-plate 31, 33 may be a perforated plate, similar to the perforated plate 230, and include independent vacuum chambers 32 for suctioning the tissue mass. The sub-plates may include a hinge 35, for example, that allows the sub-plates to fold back from the patient when not needed. In addition, when folded into place, the sub-plates 31, 33 may be configured to lock, such that the combination of the sub-plates 31, 33 are rigid and form a solid base for holding the tissue and supporting exact tissue dissection. The sub-plates 31, 33 may further include one or more support posts 37 that extend between the perforations 52 in the vacuum chamber 32.

Figure 10:
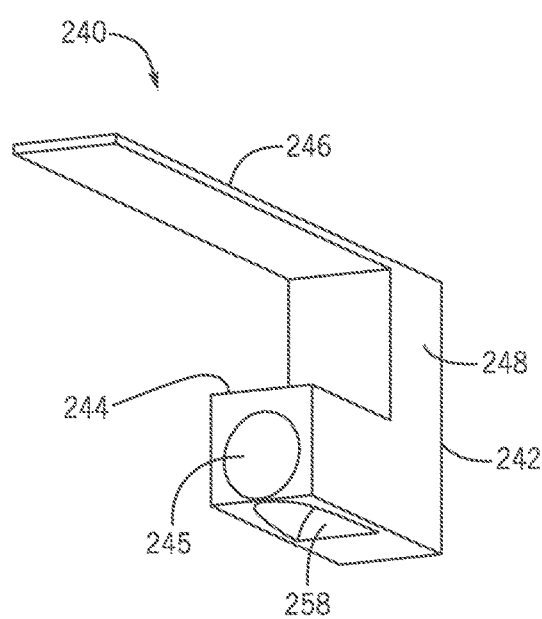
FIG. 10 is a perspective view of the tool holder of FIG. 8 including a base, a tool holder plate, and a guide arm according to one embodiment of the present invention.

Turning now to FIG. 10, the tool holder 240 is shown. As previously described, the tool holder tongue 246 of the tool holder 240 is configured to translate and rotate within the predefined plane 238 defined by the slot 236 of the guide plate 218 so that the tip 250 of the cutting tool 214, as shown in FIG. 8, moves in a defined planar region to cut the tissue flap with the substantially uniform thickness 212. The tool holder tongue 246 may be inserted into the slot 236 of the guide plate 218 from a direction away from a cutting plane 272 such that the tool holder 240 and cutting tool 214 may be introduced to the desired position relative to the tissue mass.

Alternatively, the tool holder plate 246, the tissue holder plate 216, and the guide plate 218 may be in the shape of a half cylinder, for example, so that as the tool holder 240 translates within the predefined half-cylinder 238, the tissue flap being cut more closely conforms to the three-dimensional shape of the tissue. The tool holder plate 246 may be any suitable size (e.g., 1 inch by 1 inch, or 2 inches by 1 inch) and geometric shape (e.g., square, rectangular or circular) to allow movement within the area defined by the slot 236 of the guide plate 218. Further, the tool holder 240 can be constructed of any suitable medical grade material such as plastic, titanium or rubber polymers. The size and shape of the tool holder 240 may be adjusted according to the particular surgical procedure, the anatomy of the patient or the needs of the tissue mass fixation.

The guide arm 244 of the tool holder 240 may include the aperture 245, for example a circular aperture, and a cord slot 258 configured to receive a base 260 of the cutting tool 214 and a cord 262 of the cutting tool 214, as shown in FIG. 8, respectively. As previously described, the tool holder 240 may be custom fabricated based on the cutting tool 214. The shape of the aperture 245, the cord slot 258, and the guide arm 244 may vary depending on the type of cutting tool 214 being used (i.e., a scalpel, an electrosurgical tool, a pencil, or a Bovie knife). Alternatively, the guide arm 244 may be a clamp or other mechanical attachment. The guide arm 244 may be integrally coupled to the base 242, for example, of the tool holder 240 to form a predetermined angle 264 at which the cutting tool 214 is held, as shown in FIG. 8, with respect to the tissue mass. The predetermined angle 264 can be adjusted, for example, by the geometric design of the guide arm 244 and how the guide arm 244 is attached to the base 242.

Figure 11A:
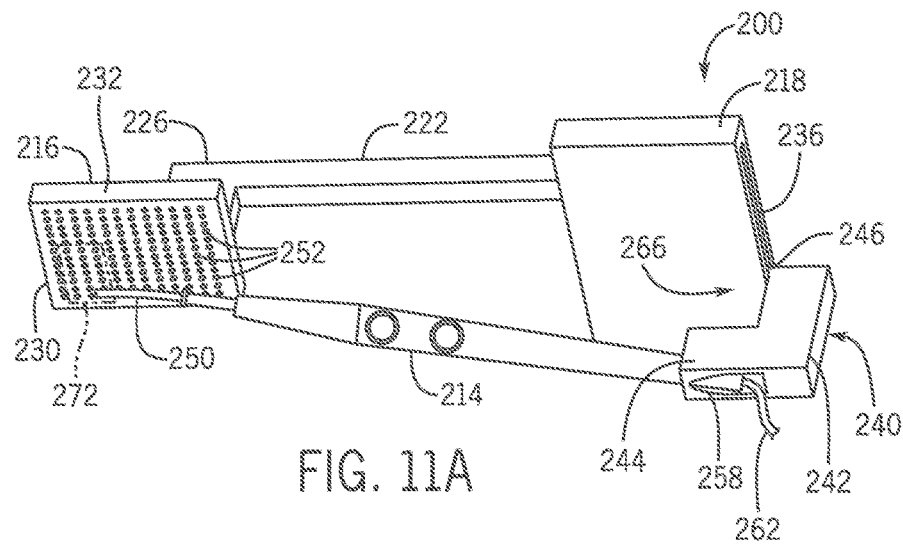
FIGS. 11A-11D are perspective views of the tool holder of FIG. 8 being translated within a predefined plane of the guide plate according to one embodiment of the present invention.
Figure 11B:
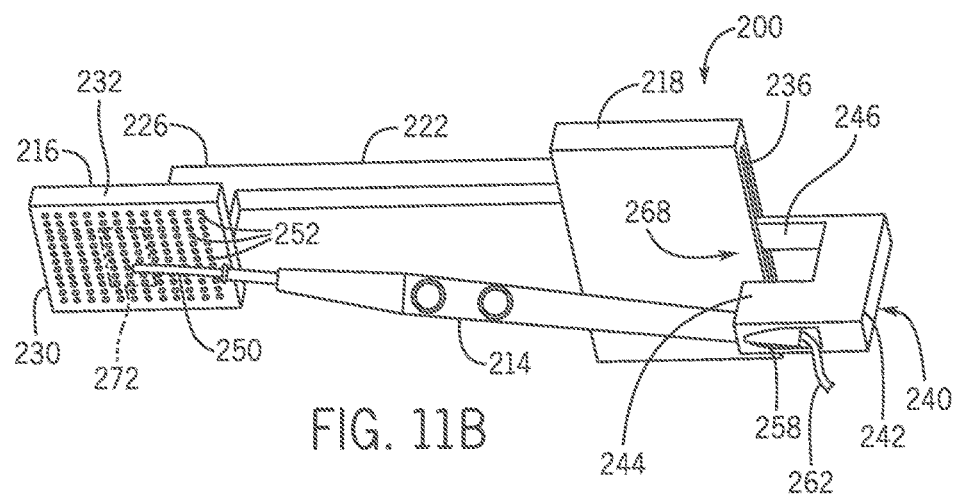
Figure 11C:
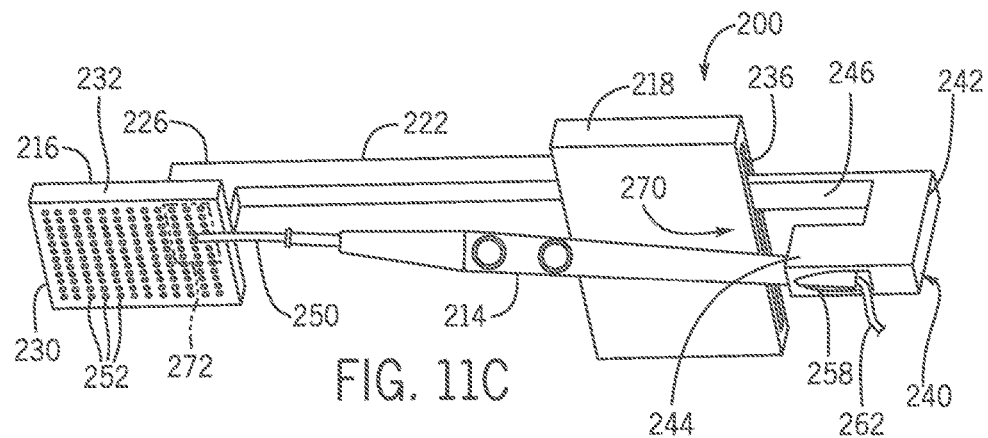
Figure 11D:
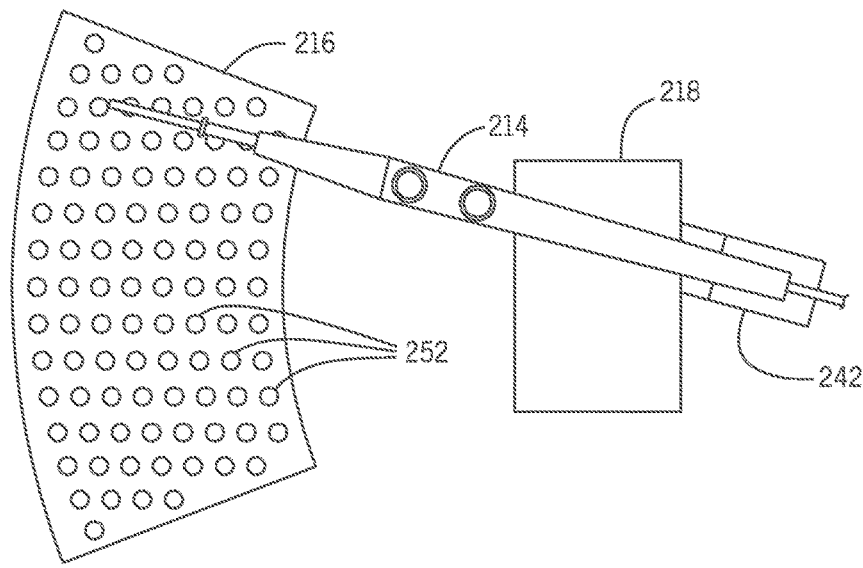

Turning now to FIGS. 11A-11D illustrations of the relative motion of the tool holder 240, and more specifically, the tool holder plate 246, in the predefined plane 238 with respect to the guide plate 218 and the tissue holder plate 216 is shown. As the tool holder 240 is moved from a first position 266, as shown in FIG. 11A, in the predefined plane 238, to a second position 268, as shown in FIG. 11B, for example, the tool holder plate 246 slides relative to the slot 236 of the guide plate 218 while maintaining the substantially uniform thickness 212 of the tissue flap. The tool holder 240 may be moved from the second position 268, as shown in FIG. 11B to a third position 270, as shown in FIG. 11C, for example while still maintaining the substantially uniform thickness 212 of the tissue flap being cut by the cutting tool 214. As the tool holder 240 is moved among the exemplary positions, the tool holder 240 may also be rotated, as shown in FIG. 11D, within the predefined plate 238 while maintaining the substantially uniform thickness 212 of the tissue flap. Also shown in FIG. 11D is the tissue holder plate 216 having a non-rectangular shape which may be advantageous for certain procedures.

In addition, as the tool holder 240 is moved among the exemplary positions, as shown in FIGS. 11A-11D, within the predefined plane 238, a cutting plane 272 is defined about the tissue mass being held in place by the tissue holder plate 216. The cutting plane 272 is therefore defined by the relative dimensions of the tool holder plate 246 and the slot 236 of the guide plate 218. It will be appreciated that the relative size of the cutting plane 272 can be varied according to the selected dimensions of slot 236 of the guide plate 218 or the tool holder plate 246, or a combination thereof.

In an alternative embodiment, the guide plate 218 and the tool holder plate 246 may be attached such that they remain in approximation while the tool holder 240 is moved among the first position 266, the second position 268, and the third position 270, as shown in FIGS. 11A, 11B and 11C, respectively. Note, however, the tool holder 240 is not restricted to the positions shown in FIGS. 11A-11C, but may move to any position within the predefined plane 238. Thus, the guide plate 218 remains in approximation with the tissue holder plate 216 while allowing free motion within the predefined plane 238.

Figure 12:
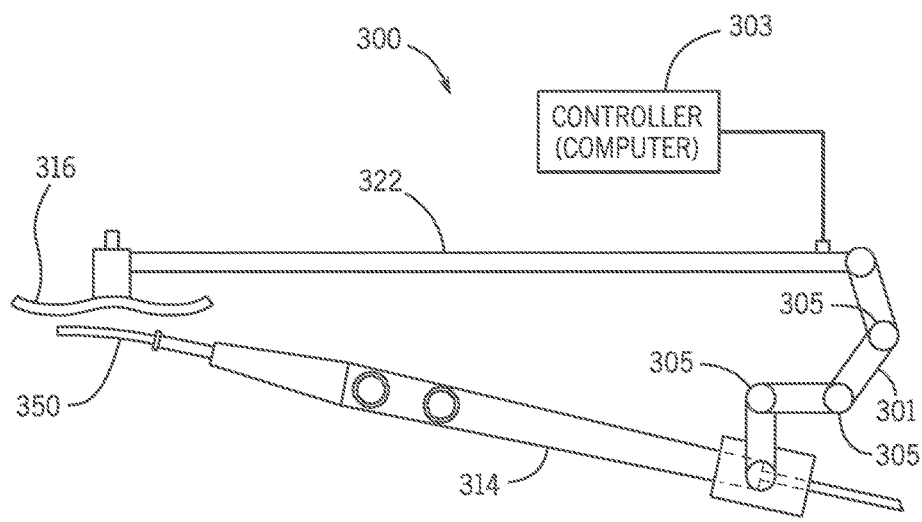
FIG. 12 is a perspective view of the example surgical device of FIG. 8 according to one embodiment of the present invention.

Turning now to FIG. 12, another embodiment of a surgical device 300 is shown. The surgical device 300 may include one or more of the features as described with respect to the surgical devices 10 and 200. Thus, similar reference numerals are used to describe the components and features of the surgical device 300 shown in FIG. 12 as were used to describe the surgical devices 10 and 200. The surgical device 300 may additionally include a robot, for example, to maintain the predetermined tissue thickness rather than relying on the mechanical constraint of the tongue and slot system.

As shown in FIG. 12, the movement of the cutting tool 314 relative to the tissue holder plate 316 may be accomplished by electro-mechanical (i.e.; robotic) means. In the embodiment shown in FIG. 12, the tool 314 is moved according to a multi-degree-of-freedom computer controlled actuator 301 that is in communication with a controller computer 303. In one example, the surgical device 300 may have a six degree-of-freedom tracking of the tissue holder plate 316 and the tool 314 motion with respect to a common coordinate frame of reference, using techniques such as optical tracking, magnetic tracking, or through encoders at each joint 305 of the articulated electromechanical arm 301. The computer controller 303 may have stored thereon a control algorithm to impose virtual fixture constraints that prevent the tool 314 from moving outside of a predefined range of motion. Additionally, or alternatively, the articulated electromechanical arm 301 may include force sensors (not shown), to allow an operator to freely move the arm 301 within the constrained geometry while inhibiting motion outside of it. Thus, in this embodiment, it is possible to create a tissue holder plate 316 with any patient-specific and/or procedure specific surface suitable for the surgical procedure. Additionally, or alternatively, the tissue holder plate 316 may be mounted on a similar electro-mechanical arm (not shown) so that its motion can be coordinated with the tool 314 under the control of the controlling computer 303. Motion of the tissue holder plate 316 would allow, as a non-limiting example, for the dissected skin tissue to be pulled away from the underlying breast tissue during mastectomy in order to better expose the cutting surface.

As described earlier, well known medical imaging technologies such as CT and MR scans can be used to make detailed maps of the patient anatomy, and in particular the scans can be used to identify critical structures and to inform clinical decision making in order to optimize surgical plans. An aspect of the current invention is the ability to incorporate information from these scan into the algorithm running on the controlling computer 303 such that the surgeon is informed during the procedure based on information derived from the images. As a non-limiting example, MR or CT angiographic imaging could be used to determine the location of blood vessels and the controlling computer 303 could be programmed to activate an auditory and/or visual alert when the cutting tool is approaching a blood vessel.

In another embodiment of the present invention, active sensors may be incorporated into the tissue holder plate 316 or tool 314 to provide real-time monitoring of the procedure. As a non-limiting example, optical sensors may be used to measure blood perfusion in the tissue as a way of monitoring tissue flap viability. Other sensors such as ultrasonic, thermal, or mechanical sensors could also be incorporated into the tissue holder plate 316 to provide additional channels of information to support the surgical procedure.

Thus, the above described system and method allows for tissue flap dissection of substantially uniform thickness in non-anatomic planes. The systems and methods further allow for precise gaging of tissue flap dissection, thereby reducing the surgeon's margin of error and patient morbidity.

The present invention has been described in terms of one or more preferred embodiments, and it should be appreciated that many equivalents, alternatives, variations, and modifications, aside from those expressly stated, are possible and within the scope of the invention.

The invention claimed is:

1. A surgical device for preparing a tissue flap from a tissue mass, the surgical device comprising:
    a guide plate including at least one of a peripheral ridge and a slot;
    a tissue holder plate configured to securely hold the tissue mass a predetermined distance from and orientation to the guide plate;
    a support member coupled between the guide plate and the tissue holder plate; and
    a tool holder configured to receive a cutting tool for cutting the tissue flap from the tissue mass, the tool holder comprising:
    a base;
    a tool holder plate coupled to the base, the tool holder plate dimensioned to engage the guide plate and translate and rotate within the at least one peripheral ridge and slot to restrict movement of the cutting tool to a predefined plane relative to the tissue mass and the tissue holder plate;
    a guide arm coupled to the base of the tool holder at a predetermined angle relative to the tool holder plate and configured to engage the cutting tool; and
    wherein movement of the tool holder plate within the at least one peripheral ridge and slot of the guide plate enables the cutting tool to cut the tissue mass in the predefined plane at the predetermined angle, thereby preparing a tissue flap with a substantially uniform predetermined thickness from the tissue mass.

2. The surgical device as recited in claim 1, wherein the cutting tool is at least one of a scalpel, an electrosurgical tool, a pencil, a scissors and a Bovie knife.

3. The surgical device as recited in claim 1, wherein the tissue holder plate includes a perforated plate and a the vacuum chamber, thereby providing suction to hold the tissue mass in place.

4. The surgical device as recited in claim 3, wherein the perforated plate includes a plurality of suction cups coupled to perforations defined by the perforated plate, the plurality of suction cups configured to secure the tissue mass to the tissue holder plate.

5. The surgical device as recited in claim 3, further comprising at least one of a gel, glue, and a double-sided adhesive patch applied to at least one of the tissue mass and the tissue holder plate to secure the tissue mass to the tissue holder plate.

6. The surgical device as recited in claim 3, further comprising a valve system coupled to a vacuum hose attachment to control the suction provided by the vacuum chamber.

7. The surgical device as recited in claim 1, wherein the base of the tool holder includes a cord slot configured to receive a cord for powering the cutting tool.

8. The surgical device as recited in claim 1, wherein the base of the tool holder includes an aperture configured to receive a base of the cutting tool.

9. The surgical device as recited in claim 1, wherein at least one of the guide plate, the tissue holder plate, the base, the tool holder plate, and the guide arm are interchangeable with sized replacements matched to at least one of a patient size, a tissue flap size, and a surgical procedure.

10. The surgical device as recited in claim 1, further including a cutting plane defined by the dimensions of the guide plate and the tool holder plate, wherein the dimensions of the guide plate and the tool holder plate determine the relative size of the predefined plane.

11. The surgical device as recited in claim 1, wherein the tissue flap is prepared for at least one of a mastectomy, a reconstructive surgery, a thin flap evaluation in mastectomy, and a general flap elevation.

12. The surgical device as recited in claim 1, wherein the support member is an ergonomic handle adapted for a plurality of tissue flap sizes manipulated by the surgical device.

13. The surgical device as recited in claim 1, wherein the predetermined angle of the guide arm determines the substantially uniform thickness of the tissue flap in the predefined plane.

14. The surgical device as recited in claim 1, further including a linkage configured to attach the guide plate and the tool holder plate, thereby enabling movement of the tool holder plate relative to the guide plate in the predefined plane.

15. The surgical device as recited in claim 14, wherein the linkage includes a magnet embedded within the tool holder plate configured to magnetically attract the guide plate.

16. The surgical device as recited in claim 1, wherein the guide plate and the tool holder plate include a planar surface.

17. The surgical device as recited in claim 1, wherein the guide arm is at least one of a cylindrical cut out, a clamp, and a mechanical attachment.

18. The surgical device as recited in claim 1, further including a sliding linkage coupled to the base of the tool holder and the guide arm, thereby forming an adjustable system to select the substantially uniform thickness of the tissue flap by vertically sliding the sliding linkage.

19. The surgical device as recited in claim 1, wherein at least one of the tool holder plate, the tissue holder plate, and the guide plate has a partial cylinder shape, thereby enabling the predefined plane to be non-linear.

* * * * *